US012589177B2

(12) United States Patent
    Edgerly

(10) Patent No.: US 12,589,177 B2
(45) Date of Patent: Mar. 31, 2026

(54) APPARATUS AND METHOD FOR MOLD AND MYCOTOXIN REMEDIATION

(71) Applicant: Sheryl Edgerly, Salt Lake City, UT (US)

(72) Inventor: Sheryl Edgerly, Salt Lake City, UT (US)

( * ) Notice: Subject to any disclaimer, the term of this patent is extended or adjusted under 35 U.S.C. 154(b) by 961 days.

(21) Appl. No.: 17/525,014

(22) Filed: Nov. 12, 2021

(65) Prior Publication Data

US 2022/0152263 A1     May 19, 2022

Related U.S. Application Data

(60) Provisional application No. 63/113,315, filed on Nov. 13, 2020.

(51) Int. Cl.
    *A61L 9/16*         (2006.01)
(52) U.S. Cl.
    CPC ............. *A61L 9/16* (2013.01); *A61L 2209/11* (2013.01); *A61L 2209/15* (2013.01)
(58) Field of Classification Search
    CPC ................................... A61L 2/025; A61L 9/16
    See application file for complete search history.

(56) References Cited

U.S. PATENT DOCUMENTS

| | | | |
|---|---|---|---|
| 8,991,259 B2 * | 3/2015 | Laugharn, Jr. ......... | B01J 19/006 |
| | | | 435/6.12 |
| 10,799,914 B2 * | 10/2020 | Savage .................. | C12N 1/066 |
| 2004/0161362 A1 * | 8/2004 | Bogert ...................... | A61L 2/02 |
| | | | 422/1 |
| 2010/0113983 A1 * | 5/2010 | Heckerman .............. | A61N 7/00 |
| | | | 601/2 |
| 2020/0209138 A1 * | 7/2020 | Yee .................... | G01N 15/0656 |

* cited by examiner

*Primary Examiner* — Donald R Spamer
*Assistant Examiner* — Kayla Rose Sarantakos
(74) *Attorney, Agent, or Firm* — Mohr Intellectual Property Law Solutions, PC

(57) ABSTRACT

A system and method for a mold and mycotoxin remediation system and method is provided. One embodiment serially accesses each one of a plurality of acoustic energy clips that are configured to kill a mold or eliminate a mycotoxin of interest, generates an acoustic energy content signal based on the acoustic energy information of the serially accessed plurality of acoustic energy clips, communicates the generated acoustic energy content signal to a speaker, wherein the speaker emits acoustic energy based on the communicated acoustic energy content signal such that the emitted acoustic energy kills mold or eliminates mycotoxins.

19 Claims, 3 Drawing Sheets

100

402

| Name | Date Modified |
|---|---|
| ♫ 01 MW4-1 Molds T-1 2.mp3 | May 13, 2020 |
| ♫ 01 MW4-1 Molds T-1.mp3 | May 13, 2020 |
| ♫ 02 MW4-1 Mycos-2.mp3 | May 13, 2020 |
| ♫ 03 MW4-1 Mycos-6.mp3 | May 13, 2020 |
| ♫ 04 MW4-1 Mycos-12.mp3 | May 13, 2020 |
| ♫ 05 MW4-2 Molds T-2 2.mp3 | May 13, 2020 |
| ♫ 05 MW4-2 Molds T-2.mp3 | May 13, 2020 |
| ♫ 06 MW4-2 Mycos-3.mp3 | May 13, 2020 |
| ♫ 07 MW4-2 Mycos-5.mp3 | May 13, 2020 |
| ♫ 08 MW4-2 Mycos-7.mp3 | May 13, 2020 |
| ♫ 09 MW4-3 Molds G-3 2.mp3 | May 13, 2020 |
| ♫ 09 MW4-3 Molds G-3.mp3 | May 13, 2020 |
| ♫ 10 MW4-3 Mycos-1.mp3 | May 13, 2020 |
| ♫ 11 MW4-3 Mycos-9.mp3 | May 13, 2020 |
| ♫ 12 MW4-4 Molds HH-4.mp3 | May 13, 2020 |
| ♫ 13 MW4-4 Molds HH-4 4min.mp3 | May 13, 2020 |
| ♫ 14 MW4-4 Mycos-8.mp3 | May 13, 2020 |
| ♫ 15 MW4-4 Mycos-11.mp3 | May 13, 2020 |
| ♫ 16 MW4-5 Molds GL-5.mp3 | May 13, 2020 |
| ♫ 17 MW4-5 Mycos-10.mp3 | May 13, 2020 |
| ♫ 18 MW4-6 Molds YS-6.mp3 | May 13, 2020 |
| ♫ 19 MW4-6 Mycos-4.mp3 | May 13, 2020 |
| ♫ 20 MW4-7 MT-7.mp3 | May 13, 2020 |

MEMORY

~122

~104

APPARATUS AND METHOD FOR MOLD AND MYCOTOXIN REMEDIATION

PRIORITY CLAIM

This application claims priority to U.S. Provisional Application, Ser. No. 63/113,315, filed on Nov. 13, 2020, entitled Systems and Methods For APPARATUS AND METHOD FOR MYCOTOXIN REMEDIATION, which is hereby incorporated by reference in its entirety for all purposes.

BACKGROUND OF THE INVENTION

In the art of mold remediation, and in particular for killing mold and eliminating mycotoxins in an enclosed environment such as a home or other structure, mold remediation can be an extremely complicated, expensive, and potentially dangerous process.

Accordingly, there is a need in the art to provide an improved mold and mycotoxin remediation process and system that can kill mold and eliminate mycotoxins without scrubbing, cleaning, fogging, or the use of toxic chemicals.

SUMMARY OF THE INVENTION

Embodiments of the mold and mycotoxin remediation system and method kills mold or eliminates mycotoxins. One embodiment serially accesses each one of a plurality of acoustic energy clips that are configured to kill a mold or eliminate a mycotoxin of interest, generates an acoustic energy content signal based on the acoustic energy information of the serially accessed plurality of acoustic energy clips, communicates the generated acoustic energy content signal to a speaker, wherein the speaker emits acoustic energy based on the communicated acoustic energy content signal such that the emitted acoustic energy kills mold or eliminates mycotoxins.

BRIEF DESCRIPTION OF THE DRAWINGS

The components in the drawings are not necessarily to scale relative to each other. Like reference numerals designate corresponding parts throughout the several views.

DETAILED DESCRIPTION

Embodiments of the mold and mycotoxin remediation system 100 provide a system and method for mycotoxin remediation. Mycotoxins are naturally occurring toxins produced by certain molds (fungi) that can be harmful to humans and other animals.

Figure 1:
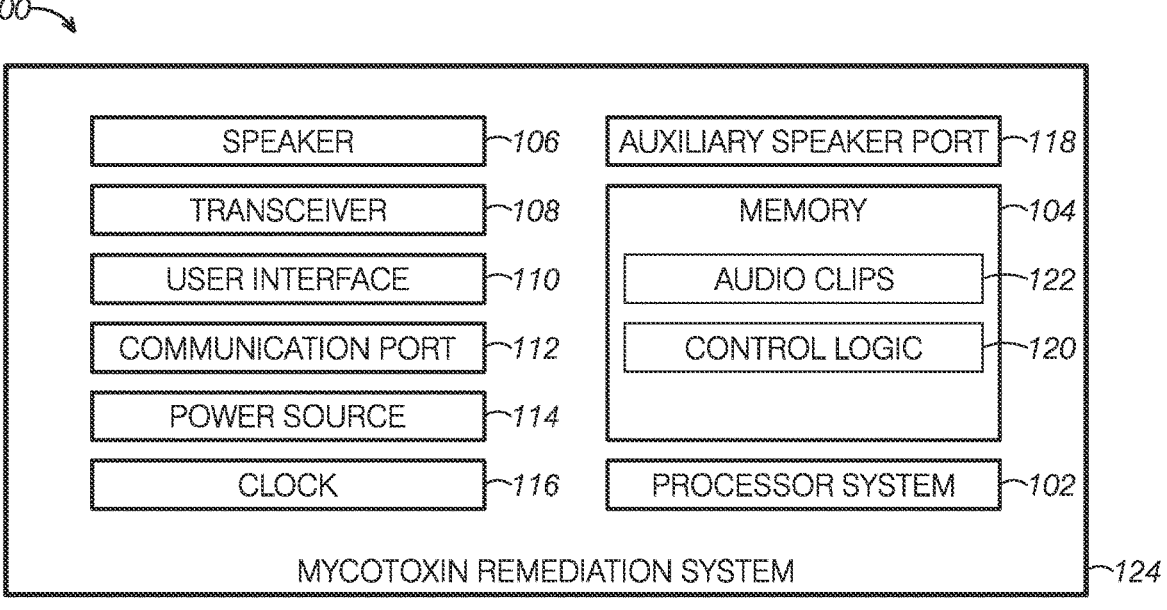
FIG. 1 is a block diagram of an embodiment of the mold and mycotoxin remediation system.

FIG. 1 is a block diagram of an embodiment of the mold and mycotoxin remediation system 100. Embodiments of the mold and mycotoxin remediation system 100 emit prerecorded acoustic energy, which may optionally include acoustic sounds, which are designed to have frequencies that kills mold that produce mycotoxins in a space in proximity to the mold and mycotoxin remediation system 100. Preferably, the mold and mycotoxin remediation system 100 is used in an enclosed, air filled environment. However, the mold and mycotoxin remediation system 100 may be used in non-enclosed environments or partially enclosed environments.

The disclosed mold and mycotoxin remediation system 100 will become better understood through review of the following detailed description in conjunction with the figures. The detailed description and figures merely provide examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various mold and mycotoxin remediation systems 100 are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components.

"Communicatively coupled" means that an electronic device is communicatively connected to another electronic device, either wirelessly or with a wire based connector, whether directly or indirectly through a communication network. "Controllably coupled" means that the electronic device is controls operation of the other electronic device.

Returning to FIG. 1, an example embodiment of a mold and mycotoxin remediation system 100 comprises a processor system 102, a memory 104, at least one speaker 106, an optional transceiver 108, a user interface 110, an optional communication port 112, a power source 114, a clock 116, and an optional auxiliary speaker port 118. The memory includes the control logic 120 and a plurality of audio clips 122. The mold and mycotoxin remediation system 100 may be enclosed in a conveniently sized case or enclosure 124 made of a rugged and durable plastic, metal, or the like.

In some embodiments, the control logic 120 may be integrated together, and/or may be integrated with other logic. In other embodiments, some or all of these memory and other data manipulation functions may be provided by using a remote server or other electronic devices suitably connected via the Internet or otherwise to a client device. Other embodiments of the mold and mycotoxin remediation system 100 may include some, or may omit some, of the above-described components. Further, additional components not described herein may be included in alternative embodiments.

The plurality of audio clips 122, interchangeably referred to herein as acoustic energy clips 122, are used to generate an audio sound clip (interchangeably referred to herein as an acoustic energy clip) that is used to generate acoustic energy that is emitted from one or more speakers 106. Each one of the plurality of audio clips 122 has acoustic energy information that has a unique predefined tonal, frequency, volume, and/or duration characteristic that is configured to kill molds and/or eliminate mycotoxins. Each clip is of a predefined duration. In a preferred embodiment, the audio clips 122 are stored as MP3 digital audio files or the like, though any suitable data format may be used without departing from the functionality of the invention. In some embodiments, the plurality of audio clips 122 may be stored in a remote electronic device and may be communicated, via the transceiver 108, to the mold and mycotoxin remediation system 100.

In operation, the user places the mold and mycotoxin remediation system 100 in the enclosed environment having mold that are to be killed and/or mycotoxins that are to be eliminated. Preferably, the enclosed environment is filled by ambient air. Alternative embodiments may be configured to operate in a liquid environment, such as water.

Preferably, the mold and mycotoxin remediation system 100 is placed in proximity to a region or area of interest that contains, or potentially contains, mold and/or mycotoxins. One skilled in the art appreciates that the effectiveness of the emitted acoustic energy will have limited range. If the region or area of interest is larger than the effective range of a single mold and mycotoxin remediation system 100, then a plurality of mold and mycotoxin remediation systems 100 may be strategically placed within the region or area to ensure effective coverage.

In some embodiments, the acoustic energy is able to penetrate materials, such as passing through paint, wall paper, wood and/or drywall. Accordingly, any mold within and/or behind the acoustic energy permeable material will be killed. Mycotoxins within and/or behind the acoustic energy permeable material will be eliminated.

After placement of the mold and mycotoxin remediation system 100 in an interior region of interest, a user actuates an on/off switch 110 to start the mold and mycotoxin remediation process. In some embodiments, an actuation command (turn on or turn off) may be generated and communicated by a remote electronic device that is received, via the transceiver 108, by the mold and mycotoxin remediation system 100 which turns on or turns off the mold and mycotoxin remediation system 100. The remotely generated actuations signal may be advantageous to concurrently control multiple mold and mycotoxin remediation systems 100. In some applications, the transceiver 108 may be configured to receive cellular signals and/or Wi-Fi signals generated by a remote electronic device, such as a smart phone or other mobile user device.

The processor system 102, executing the control logic 120, then retrieves a selected one of the plurality of audio clips 122 from the memory 104. The processor system 102 than generates an acoustic energy content signal based on the acoustic energy data (acoustic energy information) of the accessed audio clip 122. The acoustic energy content signal is communicated to the speaker(s) 106. The speaker 106 then emits acoustic energy configured to kill mold and/or eliminate mycotoxins. In some embodiments, a plurality of speakers 106 may be employed to control the effective coverage area of the mold and mycotoxin remediation system 100.

In some embodiments, the acoustic energy data in one or more of the audio clips 122 may include an audible sound that can be heard by the user. However, some audio clips 122 may not include audible sound. That is, the audible sound emitted from the speaker 106 may not be discernable by a human. In some embodiments, the audible sound heard by the user may not be configured to kill mold and/or eliminate mycotoxins, but rather be an audible indicator to the user that the mold and mycotoxin remediation system 100 is emitting acoustic energy.

Any suitable type of speaker 102 that is operable to emit acoustic energy may be used by the various embodiments. In some embodiments, the speaker 106 may be an air coil inductor or other suitable silent vibrational transducer that is configured to emit acoustic energy, and are referred to herein interchangeably as a speaker 102 for the purposes of this disclosure. Any such acoustic energy generator now known or later developed are intended to be included herein within the scope of this disclosure and protected by the following claims.

When presentation of the acoustic energy generated from the first audio clip has completed, the processor system 102 retrieves another one of the plurality of audio clips 122 from the memory 104. Then, the acoustic energy associated with that second audio clip 122 is played (emitted from the speaker 106).

In the various embodiments, a plurality of predefined audio clips 122 are selectively arranged so that they are retrieved and played in a predefined sequence. The series of audio clips 122 is interchangeably referred to as a playlist. A playlist may be used to define the order in which the series of audio clips 122 are accessed and played. In some embodiments, the playlist may define the duration of play for the specified audio clips 122. Preferably, one or more of the predefined audio clips 122 are copyrighted. Alternatively, the predefined series of audio clips 122 may be compiled into a single larger audio clip 122, referred to herein as a composite audio clip 122. In some embodiments, the predefined audio clips 122 are randomly selected during operation of the mold and mycotoxin remediation system 100. Alternatively, or additionally, audio clips 122 may be selected based on some predefined criteria that has been associated with the selected audio clip 122. As noted herein, the selected audio clips 122 may be remotely defined by a remote electronic device, and then may be communicated to the mold and mycotoxin remediation system 100 over a wireless and/or wire-based communication system for play and/or storage.

This process of repeatedly generating acoustic energy based on a plurality of sequentially accessed audio clips 122 continues for some predefined duration that is monitored by the optional clock 116. At the end of the predefined duration, the process of repeatedly generating the acoustic energy automatically ends. Alternatively, the user may manually end the process of repeatedly generating the acoustic energy.

In some embodiments, the clock 116 is an integrated component or element of the processor system 102. In an exemplary use, the audio clips 122 are presented continuously for one hour. For example, but not limited to, twenty of the audio clips 122 may be presented over the one hour presentation duration. In some embodiments, this presentation duration can be adjustable by the user via one or more controllers of the user interface 110 and/or by using a remote electronic device, such as a smart phone or the like. In some embodiments, the remote electronic device may use its own clock to monitor the predefined duration, and then issue a shut off signal to the mold and mycotoxin remediation system 100 at the in response to expiration of the predefined period.

In some embodiments, a communication port 112 is provided that is used to communicatively couple the mold and mycotoxin remediation system 100 to another electronic device, such as a computer or the like. The mold and mycotoxin remediation system 100 may be directly connected to the remote computer, and/or may be connected via a communication systems such as the internet or the like. The user may then download particular audio clips 122 of interest that are then stored into the memory 104. Alternatively, or additionally, the user may download one or more predefined playlists that may optionally be configured to be particularly effective against a particular type (species) of mold and/or mycotoxin.

The user may optionally modify the control logic to control the sequence and/or order of play of the plurality of audio clips 122. For example, the user may rearrange the sequence of presentation of audio clips 122, may define the number of audio clips 122 that are played, and/or may repeat play particular audio clips 122 depending on need. The user may input their specification using the user interface 110. Alternatively, or additionally, a remote computer and/or electronic device may include logic that is used to control and/or modify the control logic 120 of the mold and mycotoxin remediation system 100. Alternatively, or additionally, the control logic 120 may reside in the computer which is controllably coupled to the mold and mycotoxin remediation system 100.

The communication port 112 may be configured to receive an external memory device, such as a TF card or other flash memory device. Here, audio clips 122 may be downloaded from the memory device and stored into the memory 104. Alternatively, or additionally, the audio clips 122 stored on the external memory device may be directly used by the processor system 102 to generate the emitted acoustic energy. This approach may be particularly effective against a particular type (species) of mold and/or mycotoxin where the particular plurality of audio clips 122 stored on the external memory device are designed to target a particular mold and/or mycotoxin.

In embodiments with the wireless transceiver 108, the mold and mycotoxin remediation system 100 may be directly communicatively coupled to a remote electronic device via wireless communication signals 112. In such embodiments, the wireless communication system may be a low power communication system, such as a near-field communication system. An example near-field communication is Bluetooth. Any suitable low power and/or near-field communication system now known or later developed may be used in the various embodiments. A low power near-field communication system may be suitable when the mold and mycotoxin remediation system 100 is in close proximity to a remote computer or other electronic device, such as a smart phone or the mobile user electronic device. Alternatively, or additionally, other wireless communication systems may be used by the transceiver 108, such as WiFi systems, cellular telephony systems, radio systems, or the like.

Any suitable power source 114 may be used in the various alternatives. An example embodiment may use one or more rechargeable or replaceable batteries. Alternatively, or additionally, a power source may include an outlet plug configured to receive power from a conventional utility grid.

In embodiments that include the auxiliary speaker port 118, one or more auxiliary speakers (not shown) may be communicatively coupled to the mold and mycotoxin remediation system 100. Accordingly, a plurality of external speakers may be strategically placed to direct emitted mold killing and mycotoxin eliminating acoustic energy towards particular areas of interest.

In some embodiments, the speaker 106 of the mold and mycotoxin remediation system 100 may be optionally deactivated (emit no acoustic energy) while one or more auxiliary speakers are used to emit the acoustic energy. For example, but not limited to, the mold and mycotoxin remediation system 100 may be provisioned in a smart phone or other mobile user electronic device. For example, but not limited to, a smart phone may be communicatively coupled and controllably coupled to one or more auxiliary speakers that are configured to receive the acoustic energy data (acoustic energy information) generated by the smart phone or the like. Here, the audio clips 122 may be stored or accessed by the smart phone or other mobile user electronic device. For example, a smart phone, executing the control logic 120 using its smart phone processor system 102, may be used to download (via transceiver 108 and/or communication port 112) and store a plurality of audio clips 122 (in the audio clips 122 portion of its memory 104). The stored audio clips 122 may then be used to control the one or more auxiliary speakers. Alternatively, or additionally, the smart phone may be used to download the plurality of audio clips 122 which are then used to control the one or more auxiliary speakers and/or the cell phone speaker in real time. These embodiments may be particularly advantageous if specialty purpose auxiliary speakers are used to emit acoustic energy that kills mold and/or eliminates mycotoxins. Here, a consumer may purchase the specialty speakers and/or a control app (application) that is downloaded into their smart phone or the like. All such modifications and variations implemented in a smart phone or the like are intended to be included herein within the scope of this disclosure and protected by the following claims.

In some situations, different ones of the plurality of audio clips 122 may be particularly effective in killing particular types and/or species of molds. Depending upon the particular needs of the mold remedial project, selected ones of the plurality of audio clips 122 may be used to kill a particular mold type and/or species of interest. For example, some experimental tests have shown a significant decrease in certain targeted type of molds when the presentation duration was fifteen hours.

Another example embodiment is configured to kill particular types of molds and eliminate the associated mycotoxins in a greenhouse environment. One skilled in the art appreciates that molds encountered in a greenhouse are often different than typical household molds. Accordingly, the selected audio clips 122 may be predefined to target specific molds encountered in a greenhouse environment.

In practice, a series of predefined audio clips 122 may be played that target a specific mold and/or mycotoxin that may be encountered in a home, greenhouse, or other structure. Then, a plurality of different predefined audio clips 122 may be played that target a different mold. In some applications, the mold and mycotoxin remediation system 100 may be operated on a continuous basis to discourage establishment of mold in the home, greenhouse, or other structure.

Figure 2:
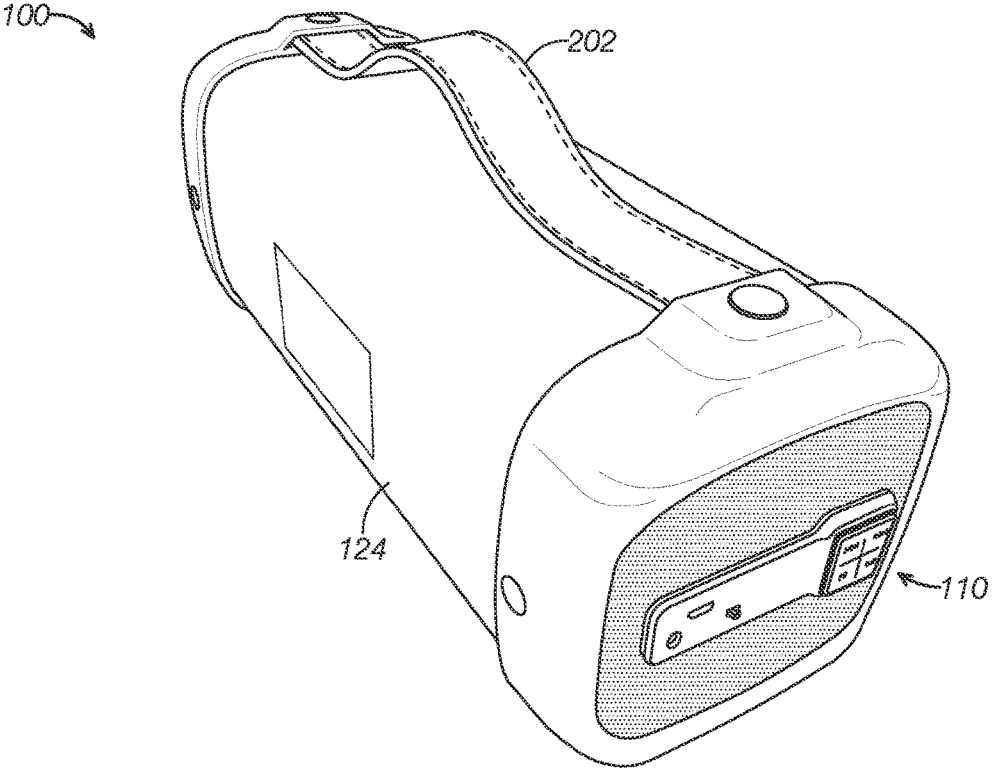
FIG. 2 is a perspective view of an embodiment of a mold and mycotoxin remediation system.

FIG. 2 is a perspective view of an embodiment of a mold and mycotoxin remediation system 100. An optional handle 202 may be secured to the exterior of the enclosure 124 to facilitate transportation and placement of the mold and mycotoxin remediation system 100 in an enclosed environment for mycotoxin remediation.

In some embodiments, the user interface 110 may include an optional on/off button that is an actuator that is designed to turn on and then turn off the mold and mycotoxin remediation system 100.

Figure 3:
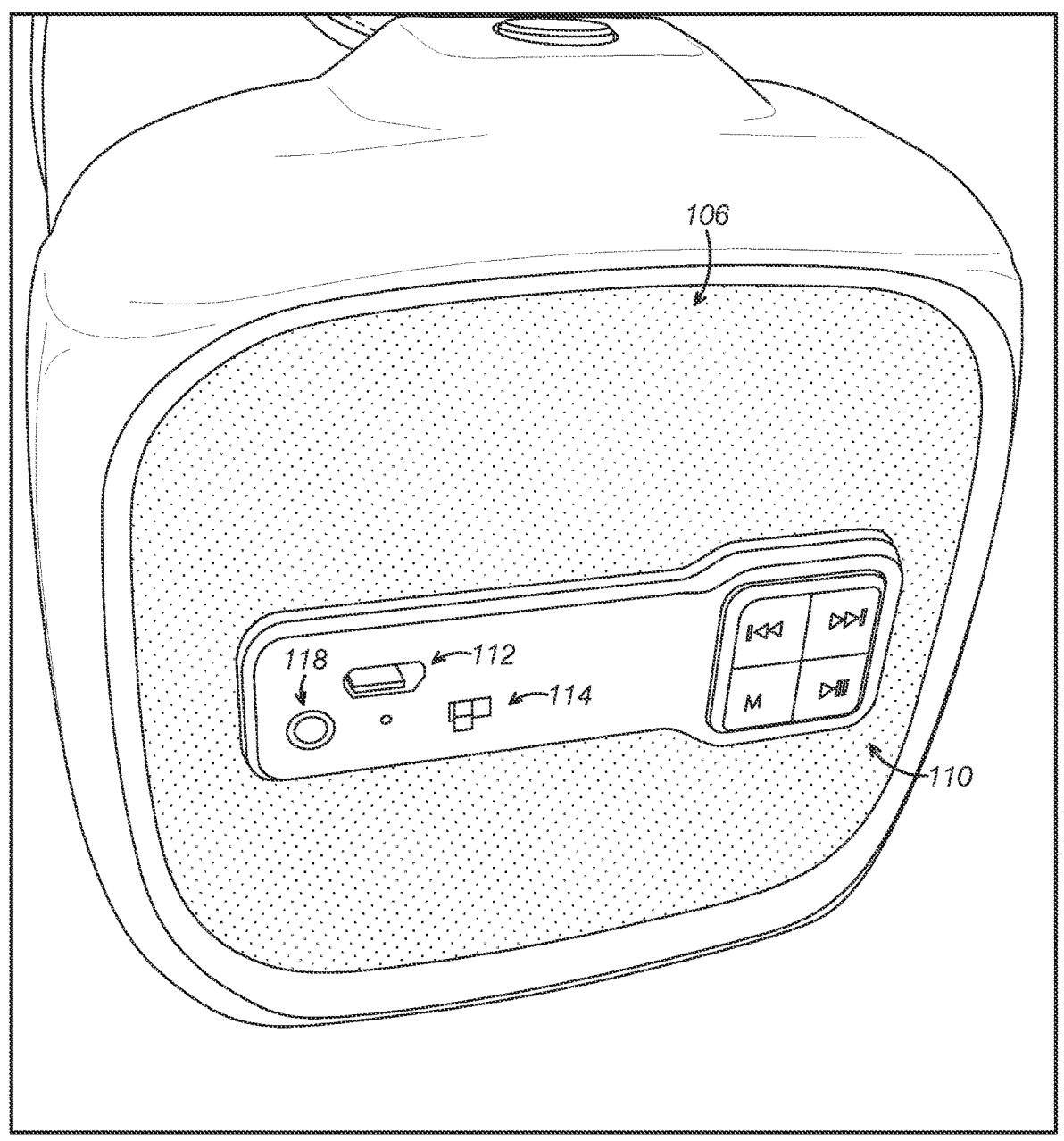
FIG. 3 is a perspective view of the front surface of an embodiment of the mold and mycotoxin remediation system.

FIG. 3 is a perspective view of the front surface of an embodiment of the mold and mycotoxin remediation system 100. A plurality of user interfaces 110 are provided on the front surface of the mold and mycotoxin remediation system 100. The user interfaces 110 may be used to control volume of the emitted acoustic energy, may be used to advance to a next audio clip 122 (denoted by the controller labeled with right pointing arrow heads), replay a current audio clip 122 (denoted by the controller labeled with left pointing arrow heads), and/or pausing current play (denoted by the controller labeled with a single right pointing arrow head). When implemented in a smart phone, the user interface 110 is implemented as a graphical user interface (GUI) that is presented on the touch sensitive display of the smart phone. Any suitable user interface device now known or later developed may be used by the various embodiments and are intended to be protected by the accompanying claims. Further, any of the user interfaces 110 may be located on any surface of interest on the mold and mycotoxin remediation system 100.

Figures 4, 5:
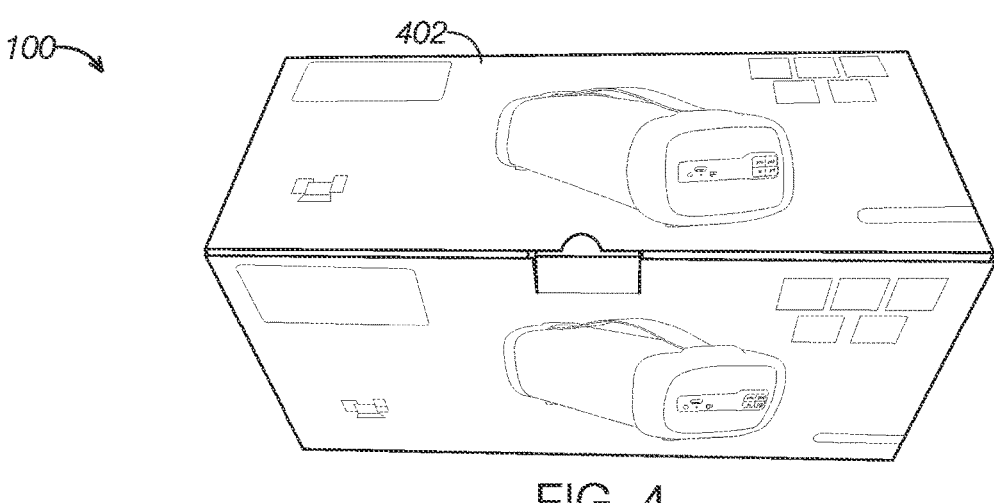
FIG. 4 is a perspective view of a delivery box that may be used deliver the mold and mycotoxin remediation system to a customer.
FIG. 5 is an exemplary listing of a plurality of sound recording clips that are used to generate audible content that remediates molds and mycotoxins in an enclosed environment.

FIG. 4 is a perspective view of a delivery box 402 that may be used deliver the mold and mycotoxin remediation system 100 to a customer. The mold and mycotoxin remediation system 100 may then be conveniently provided to purchasing consumers through a variety of retail venues.

FIG. 5 is an exemplary listing of a plurality of sound recording clips 122 that are used to generate the acoustic energy content that remediates molds and mycotoxins in an enclosed environment, such as at a home, an attic, an office, a warehouse, a greenhouse or other structure. The non-limiting example listing indicates that the audio clips 122 are stored using a relational database. Each individual audio clip 122 is identified using a unique file name. The listing may optionally indicate the file data type (here, the well-known mp3 data format). Any suitable file naming convention may be used by the various embodiments. Further, any suitable file data format suitable for storing the plurality of audio clips 122 used for generating acoustic energy may be used by the various embodiments. Any such variations now known or later developed may be used by the various embodiments and are intended to be protected by the accompanying claims.

It should be emphasized that the above-described embodiments of the mold and mycotoxin remediation system 100 are merely possible examples of implementations of the invention. Many variations and modifications may be made to the above-described embodiments. All such modifications and variations are intended to be included herein within the scope of this disclosure and protected by the following claims.

Furthermore, the disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower, or equal in scope to the original claims, are to be considered within the subject matter of the inventions described herein.

The invention claimed is:

1. A mold and mycotoxin remediation method, comprising:

accessing from a memory a first one of a plurality of acoustic energy clips, wherein the first acoustic energy clip includes acoustic energy information that is configured to kill a mold or eliminate a mycotoxin of interest in a structure;

generating a first acoustic energy content signal based on the acoustic energy information of the accessed first acoustic energy clip;

communicating the generated first acoustic energy content signal to a speaker configured to produce audible sound;

placing the speaker in a position spaced from the structure with ambient air disposed between the speaker and the structure; and emitting first acoustic energy from the speaker through the ambient air towards the structure based on the communicated first acoustic energy content signal, wherein the emitted first acoustic energy is audible and kills mold or eliminates mycotoxins within the structure.

2. The mold and mycotoxin remediation method of claim 1, further comprising:

accessing from the memory a second one of a plurality of acoustic energy clips after the first acoustic energy has been emitted by the speaker, wherein the second acoustic energy clip includes acoustic energy information that is configured to kill the mold or eliminate the mycotoxin of interest in a structure;

generating a second acoustic energy content signal based on the acoustic energy information of the accessed second acoustic energy clip;

communicating the generated second acoustic energy content signal to a speaker spaced from the structure with ambient air disposed between the speaker and the structure and configured to produce audible sound; and emitting second acoustic energy from the speaker through the ambient air towards the structure based on the communicated second acoustic energy content signal, wherein the emitted second acoustic energy is audible and kills mold or eliminates mycotoxins within the structure.

3. The mold and mycotoxin remediation method of claim 2, further comprising:

serially repeating the process of:

accessing from the memory a next one of a plurality of acoustic energy clips after previous acoustic energy has been emitted by the speaker, wherein the next acoustic energy clip includes acoustic energy information that is configured to kill the mold or eliminate the mycotoxin of interest in a structure;

generating a next acoustic energy content signal based on the acoustic energy information of the accessed next acoustic energy clip;

communicating the generated next acoustic energy content signal to a speaker spaced from the structure with ambient air disposed between the speaker and the structure and configured to produce audible sound; and emitting next acoustic energy from the speaker through the ambient air towards the structure based on the communicated next acoustic energy content signal.

4. The mold and mycotoxin remediation method of claim 3, wherein the serially repeating process concludes after a predefined duration.

5. The mold and mycotoxin remediation method of claim 3, wherein the serially repeating process concludes after a predefined number of the plurality of acoustic energy clips has been accessed from the memory.

6. The mold and mycotoxin remediation method of claim 3, wherein the serially repeating process concludes in response to receiving a signal communicated from a remote electronic device.

7. The mold and mycotoxin remediation method of claim 1, further comprising:

receiving the plurality of acoustic energy clips at a communication port of a mold and mycotoxin remediation system that have been communicated from a remote electronic device; and storing the received plurality of acoustic energy clips into the memory of the mold and mycotoxin remediation system.

8. The mold and mycotoxin remediation method of claim 1, wherein the process of generating and communicating the first acoustic energy content signal is performed by a smart phone, the method further comprising:

receiving the plurality of acoustic energy clips at a communication port of the smart phone that have been communicated from a remote electronic device.

9. The mold and mycotoxin remediation method of claim 8, further comprising:

storing the received plurality of acoustic energy clips into the memory of the smart phone.

10. The mold and mycotoxin remediation method of claim 8, wherein the plurality of acoustic energy clips are received at the smart phone one at a time from the remote electronic device, and wherein a series of acoustic energy content signals are generated and communicated to the speaker as each one of the serially communicated plurality of acoustic energy clips are received at the smart phone.

11. The mold and mycotoxin remediation method of claim 10, wherein the process of generating and communicating the series of acoustic energy content signal to the speaker concludes when a last one of the plurality of acoustic energy clips is received at the smart phone.

12. The mold and mycotoxin remediation method of claim 8, where the speaker is an external speaker that is communicatively coupled to the smart phone.

13. The mold and mycotoxin remediation method of claim 1, wherein the process of generating and communicating the first acoustic energy content signal is performed by a mold and mycotoxin remediation system, the method further comprising:

receiving the plurality of acoustic energy clips at a communication port of the mold and mycotoxin remediation system that have been serially communicated from a smart phone.

14. The mold and mycotoxin remediation method of claim 1, wherein the process of generating and communicating the first acoustic energy content signal is performed by a mold and mycotoxin remediation system, the method further comprising:

receiving the plurality of acoustic energy clips at a communication port of the mold and mycotoxin remediation system, wherein the memory is an external memory that is communicatively coupled to the mold and mycotoxin remediation system via the communication port.

15. The mold and mycotoxin remediation method of claim 1, wherein the speaker is one of a plurality of external speakers, the method further comprising:

communicating the generated first acoustic energy content signal to the plurality of external speakers, wherein the first acoustic energy is emitted from the plurality of external speakers based on the communicated first acoustic energy content signal.

16. A mold and mycotoxin remediation system, comprising:

a memory that stores a plurality of acoustic energy clips that each include acoustic energy information that is configured to kill a mold or eliminate a mycotoxin of interest in a structure; and a speaker spaced from the structure with ambient air disposed between the speaker and the structure and configured to produce audible sound;

a processor system communicatively coupled to the memory, wherein the processor system:

serially accesses from the memory the plurality of acoustic energy clips;

generates an acoustic energy content signal based on the acoustic energy information of the each of the serially accessed plurality of acoustic energy clips; and communicates the generated acoustic energy content signal to the speaker, wherein acoustic energy is emitted from the speaker through the ambient air towards the structure based on the communicated acoustic energy content signal, wherein the emitted acoustic energy is audible and kills mold or eliminates mycotoxins within the structure.

17. The mold and mycotoxin remediation system of claim 16, further comprising:

an auxiliary speaker port that communicatively couples the speaker to the mold and mycotoxin remediation system.

18. The mold and mycotoxin remediation system of claim 16, wherein the processor system is a smart phone processor system of a smart phone.

19. The mold and mycotoxin remediation method of claim 1, wherein:

the structure includes one or more of paint, wallpaper, wood, or drywall;

the one or more of paint, wallpaper, wood, or drywall of the structure is disposed between a mold or a myco-toxin of interest; and the acoustic energy information is configured to kill a mold or eliminate a mycotoxin of interest behind one or more of paint, wallpaper, wood, or drywall of a struc-ture; and emitting the first acoustic energy kills the mold or elimi-nates the mycotoxin of interest with one or more of paint, wallpaper, wood, or drywall of the structure disposed between the speaker and the mold or the mycotoxin of interest.

\* \* \* \* \*